United States Patent [19]

Röhrscheid et al.

[11] Patent Number: 5,274,126
[45] Date of Patent: * Dec. 28, 1993

[54] PARTIALLY FLUORINATED TETRACARBOXYLIC ACID AND THE DIANHYDRIDE THEREOF, A PROCESS FOR THEIR PREPARATION AND THEIR USE

[75] Inventors: Freimund Röhrscheid; Wolfgang Appel, both of Kelkheim; Günter Siegemund, Hofheim, all of Fed. Rep. of Germany

[73] Assignee: Hoechst AG, Frankfurt, Fed. Rep. of Germany

[*] Notice: The portion of the term of this patent subsequent to Apr. 2, 2008 has been disclaimed.

[21] Appl. No.: 893,771

[22] Filed: Jun. 5, 1992

Related U.S. Application Data

[62] Division of Ser. No. 718,020, Jun. 20, 1991, Pat. No. 5,153,334.

[30] Foreign Application Priority Data

Jun. 25, 1990 [DE] Fed. Rep. of Germany ....... 4020186

[51] Int. Cl.$^5$ .................... C07D 307/77; C07C 51/16
[52] U.S. Cl. .................................. 549/241; 562/412; 562/415; 562/416; 562/417
[58] Field of Search ................ 549/241; 562/412, 415, 562/416, 417

[56] References Cited

U.S. PATENT DOCUMENTS

| | | | |
|---|---|---|---|
| 3,355,500 | 11/1967 | Farah et al. | 260/613 |
| 4,946,935 | 8/1990 | Ohsaka et al. | 528/353 |
| 5,004,797 | 4/1991 | Rohrscheid et al. | 528/206 |

FOREIGN PATENT DOCUMENTS 0285160 10/1988 European Pat. Off. .
3739796 6/1989 Fed. Rep. of Germany .

OTHER PUBLICATIONS

Farah, B. S. et al., *J. Org. Chem.* 30:998–1001 (1965).
Colon, I. et al., *J. Org. Chem.* 51:2627–2636 (1986).

*Primary Examiner*—Cecilia Tsang
*Attorney, Agent, or Firm*—Connolly and Hutz

[57] ABSTRACT

A compound of the formula

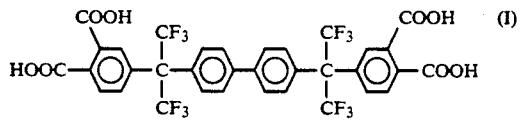

and the dianhydride thereof are prepared by air oxidation in the presence of a catalyst mixture composed of at least 2 heavy metal salts and also bromine in an acid organic medium. The compounds can be employed for the preparation of partially fluorinated polycondensates, such as polyimides, polycarboxamides, esters of polyamidecarboxylic acids, polyamides and imide-oligomers.

25 Claims, No Drawings

PARTIALLY FLUORINATED TETRACARBOXYLIC ACID AND THE DIANHYDRIDE THEREOF, A PROCESS FOR THEIR PREPARATION AND THEIR USE

This is a divisional application of Ser. No. 07/718,020 filed Jun. 20, 1991 now U.S. Pat. No. 5,153,334.

DESCRIPTION

Partially fluorinated tetracarboxylic acid and the dianhydride thereof, a process for their preparation and their use.

The invention relates to a partially fluorinated tetracarboxylic acid, in particular 4,4'-bis-[2-(3,4-dicarboxyphenyl)hexafluoroisopropyl]-biphenyl, to its dianhydride and to a process for their preparation and to their use.

The preparation of 4,4'-bis-[2-(3,4-dicarboxyphenyl)-hexafluoroisopropyl]-diphenyl ether by air oxidation in an acid medium in the presence of a catalyst mixture is known [DE-A 3,739,796].

The invention relates to a compound of the formula

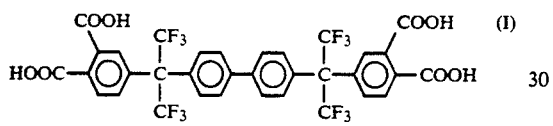

and to the dianhydride thereof, to a process for their preparation and to their use as monomer components for polycondensates, in particular polyimides.

The preparation of the compound according to the invention is effected by oxidizing a 4,4'-bis-[2-(3,4-dialkylphenyl)hexafluoroisopropyl]-biphenyl with molecular oxygen in an acid organic medium, the acid medium being composed of at least 40% by weight of a monocarboxylic acid having 1 to 4 carbon atoms, in particular acetic acid or propionic acid or mixtures thereof, in the presence of a catalyst combination composed of at least 2 heavy metal salts, in particular salts of cobalt and manganese, and also bromine. In addition, cerium ions can also be present. Acetic acid is to be preferred because of its greater stability to oxidative decomposition. The ratio of the acid medium to the biphenyl compound to be oxidized is not higher than 40:60% by weight, relative to the total reaction mass.

The biphenyl compound employed

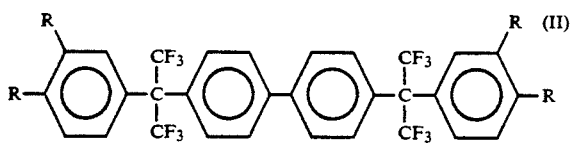

in which R is lower alkyl having 1–4 carbon atoms, alkyl being preferably methyl, ethyl and isopropyl, in particular methyl, is generally prepared by three different methods, specifically:

a) by condensation of one mole of a dicarbinol of the formula

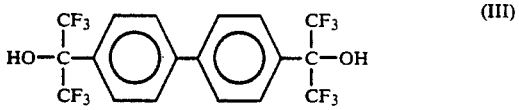

with at least 2 mol of a compound having the formula

in which R has the meaning mentioned above, or b) by condensation of at least 2 mol of a compound of the formula

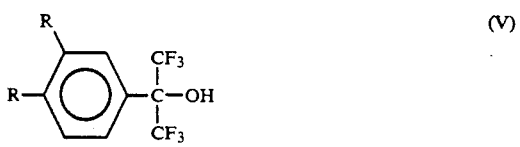

in which R has the meaning mentioned above, with one mole of biphenyl (VI), in each case in the presence of hydrogen fluoride, or c) by the formation of the carbon-carbon bond between 2 identical partially fluorinated aromatic compounds of the formula

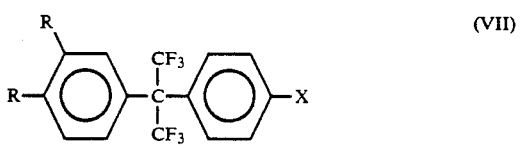

in which R has the meaning mentioned above, by a method which is known from the literature and which is suitable for the formation of aryl-aryl bonds, for example J. Org. Chem. 51, 2627 (1986).

X is halogen, preferably chlorine.

Compounds of the formula (III) employed in method a) are described in U.S. Pat. No. 3,355,500 and in J. Org. Chem. 30, 998 (1965). Compounds of the formula (V) which are reacted by method b) to give the compounds of the formula (II) are also described in J. Org. Chem. 30, 998–1001 (1965).

The reaction according to methods a) and b) is carried out at a temperature from 80° to 180° C., preferably 100° to 160° C.

A time of 20 to 90 hours, preferably 40 to 70 hours, is necessary for the reaction according to methods a) and b).

The molar ratio of the reactants employed is determined in the case of method a) by the ratio of the compound (III) to the compound (IV) and, in method b), by the ratio of the biphenyl to the compound (V); it is in each case at least 1:2, preferably 1:2.2 to 1:4.4.

The proportion of hydrogen fluoride required in the reaction for the preparation of the compounds according to formula (II) is related in the case of method a) to the compound (III) and is generally used in a molar ratio of 1:7 to 1:25, preferably 1:8 to 1:12. In the case of method b) the molar ratio of the compound (V) to hydrogen fluoride is generally 1:6 to 1:15, preferably 1:8 to 1:12.

The reaction product is generally worked up by removing, as gas, the hydrogen fluoride from the reactor after the completion of the reaction at approx. 80° C. and by removing from the reactor, preferably at a temperature of 20°-30° C., the residue which remains, if appropriate after dilution with an organic solvent.

Suitable solvents which can be used for this are aliphatic hydrocarbons having 5 to 10 carbon atoms, aromatic hydrocarbons having 6 to 8 carbon atoms and monochlorinated or polychlorinated aliphatic hydrocarbons having 1 to 4 carbon atoms in the alkyl radical. Examples of these are n-hexane, n-heptane, toluene, the various xylenes, methylene dichloride and chloroform, preferably toluene, methylene dichloride or chloroform.

Water is added to the crude mixture obtained, which is washed and separated off. In general, the purified products are obtained in the form of colorless crystals.

The reaction product can be purified further by being subjected to recrystallization from an organic solvent or by being extracted by stirring in organic solvents, preferably in isopropanol, methanol or 1-chloropropane.

The preparation of the compound shown in formula (VII) can be effected by known methods from compounds of the formula (V) and aryl halides.

The formation of the aryl-aryl bond between two components of the formula (VII) is carried out in a polar, aprotic solvent, such as dimethylacetamide or dimethylformamide, in the presence of a mixture of 1 to 10 mol %, preferably 3 to 6 mol %, of a nickel(II) salt, preferably $NiCl_2$ or $NiBr_2$, and 5 to 40 mol %, preferably 20 to 30 mol %, of an organic phosphorus (III) compound, preferably triphenylphosphine, and zinc powder in a ratio of 120 to 160 mol %, relative to the aryl halide employed.

The reaction is carried out in an inert gas atmosphere, particularly nitrogen or argon, at a temperature of 40° to 80° C.; the reaction takes 2 to 8 hours.

The solid fraction is filtered off and, after the addition of a water-immiscible solvent, for example a monochlorinated or polychlorinated aliphatic hydrocarbon having 1-4 carbon atoms in the alkyl radical, in particular methylene dichloride or chloroform, ethyl acetate or diethyl ether, the filtrate is washed several times with water. Separation of the phases takes place. After the organic phase has been dried, the solvent is distilled off and the residual product is purified by recrystallization.

Bromide ions are absolutely necessary for the oxidation to proceed to completion. The two heavy metal salts, in particular those of cobalt and manganese, are generally employed in a ratio of 3:1 to 1:3, preferably 1:1. The sum of the concentrations of the two cations is generally 0.01 to 0.2, preferably 0.02 to 0.12 and particularly 0.04 to 0.08, gram.atoms/kg of total mass. The ratio of the sum of the metal salts, preferably those of cobalt and manganese, to bromine is generally 1:0.01 to 1:0.8, preferably 1:0.05 to 1:0.4.

It is also possible to employ cerium ions in addition to the two metal ions of the catalyst. The cerium ions catalyze the oxidation of incompletely oxidized intermediate stages. Their presence increases the purity and the yield of the partially fluorinated tetracarboxylic acid. The cerium ions are added to the catalyst in a ratio, of the sum of the cobalt and manganese ions to cerium ions, such as 1:0.02 to 1:1.2, preferably 1:0.05 to 1:0.6.

If a mixture of the metal ions of cobalt and cerium is used, the molar ratio of the two metals is generally 1:0.02 to 1:1.2, the ratio of the metals to bromine being as described above. The molar ratios relate in each case to the total mass, i.e. to the sum of the compound to be oxidized, the solvent and the catalyst. It is preferable to employ the corresponding acetates as the metal salts.

Bromine can be employed in the form of bromides, for example the bromides of the alkali metals including ammonium bromide and of the metals cobalt, manganese and cerium, or in the form of a solution of hydrogen bromide in water or glacial acetic acid. It is also possible to use bromine-containing organic compounds which decompose during the oxidation and liberate bromine ions, for example carbon tetrabromide.

The oxidation is generally carried out at a temperature of 120° to 220° C., preferably 140° to 190° C. and especially 155° to 180° C. The pressure in the reactor is generally 5 to 40, preferably 10 to 30 and particularly 14 to 20, bar.

It is advantageous for the process that the air required for the oxidation should be introduced into the liquid phase near to the base of the reactor and it should preferably be finely distributed in the liquid phase by means of vigorous stirring or by means of special nozzles. It is particularly advantageous to use an oxidation mixture the oxygen content of which has been increased to a content of over 21% by volume by the admixture of pure oxygen. High oxygen partial pressures are obtained by this measure in the gas bubbles entering the liquid phase. It is advantageous if the oxygen partial pressure at the outlet point of the introduction device is at least 1 bar, preferably 2 to 15 bar and particularly 3 to 10 bar.

It is also advantageous for carrying out the process that the residual oxygen content of the exit gas should not fall below specific values. The oxygen partial pressure is defined by the formula $$P_{o2} = \% \text{ by volume of } O_2 \times (P_{total} - P_{acetic})$$

i.e. it is the mathematical product of the residual oxygen content and the difference between the total pressure and the vapor pressure of acetic acid at the ambient reaction temperature. This oxygen partial pressure in the gas phase over the reaction solution should not fall below 0.2 bar and is preferably 0.35 to 2.8 bar, in particular 0.45 to 1.3 bar.

After the completion of the strongly exothermic reaction it is advisable, in order to complete the oxidation of all the alkyl groups, to keep the reactor at 150° to 190° C., preferably 160° to 180° C., under an oxygen partial pressure of 0.4 to 2 bar, preferably 0.5 to 1.3 bar, for 1 to 3 hours, preferably for about 2 hours.

The concentration of water in the acid medium in which the reaction is carried out has an appreciable influence on the performance of the process according to the invention.

Although the tetraalkyl compounds can also be oxidized in—for example—acetic acid having a water concentration of 15% by weight or higher, this reduces the yield and, above all, the purity of the products obtained, and the oxidation of all four alkyl groups takes place only incompletely. On the other hand it has been found that the metal ions of the catalyst are precipitated by tetracarboxylic acids and thus inactivated in anhydrous acetic acid. The range of water concentration in which the metal ions remain dissolved and in which the oxidation takes place completely is 2 to 12, preferably 2 to 7 and particularly 3 to 5, % by weight of water in the monocarboxylic acid.

For conversion into the dianhydride, the tetracarboxylic acid obtained by the process according to the invention is treated in a customary manner with acetic anhydride and isolated from the reaction solution by known methods.

The compounds according to the invention are employed in particular for the preparation of polycondensates, such as polyimides, polycarboxamides, esters of polyamidecarboxylic acids, polyamides and imide-oligomers which, inter alia, have low melting points, high solubility, low dielectric constants and improved heat stability.

EXAMPLES 1) a) 4,4'-Bis[2-(3,4-dicarboxyphenyl)hexafluoroisopropyl]-biphenyl (12F-biphenyltetracarboxylic acid)

165.6 g of 4,4'-bis[2-(3,4-dimethylphenyl)hexafluoroisopropyl]biphenyl, 2.49 g of Co(OAc)$_2$.4H$_2$O, 2.45 g of Mn(OAc)$_2$.4H$_2$O, 0.45 g of HBr, corresponding to 4.5 g of 10% strength HBr solution in glacial acetic acid, and 450 g of glacial acetic acid were placed in a one-liter autoclave equipped with a stirrer, a heating jacket, a gas inlet tube, a thermometer, a reflux condenser and a device for measuring oxygen in the exit gas line. The reaction mixture was heated to 150° C. under 16 bar pressure of nitrogen. Air was then passed in through the inlet tube located close to the base. The exothermic reaction set in immediately with absorption of oxygen, the temperature rising to 185° C. Sufficient air was passed in for the oxygen content in the exit gas to be between 5 and 9% by volume.

The exothermic reaction lasted for 1 hour. The air was then replaced by a 9:1 mixture of nitrogen and oxygen and the temperature was kept at 175° C. for a further 45 minutes by heating.

When the pasty reaction mixture had cooled to 100° C., it was taken out of the reaction vessel, cooled with stirring to 20° C. and filtered with suction. The voluminous filtercake was washed with four times 150 g of glacial acetic acid. The filtercake (530 g) (tetracarboxylic acid:acetic acid approx. 1:2) was dried in a stream of air at 70° C./65 mbar.

Yield: 176.3 g (93.9% of theory)

Melting point: 208°-212° C. (dehydration) melted completely at 270° C.

Carboxyl group content: 5.13 milliequivalents of COOH/g (calculated 5.11)

Color: beige

Analysis for C$_{34}$H$_{18}$F$_{12}$O$_8$: calculated: C 52.19%; H 2.32%; F 29.14%. found: C 52.10%; H 2.25%; F 29.30%.

2) 12F-Biphenyltetracarboxylic dianhydride

The voluminous filtercake moist with acetic acid (530 g) from the isolation of 12F-biphenyltetracarboxylic acid was put into a two-liter four-necked flask together with 200 g of glacial acetic acid. 102 g (1.0 mol) of acetic anhydride were added dropwise in the course of 30 minutes at about 85° C., with stirring. The temperature rose to 120° C. and the highly fluid suspension was kept at this temperature for one hour (6% by weight of acetic anhydride in the glacial acetic acid).

The reaction solution was cooled to 20° C. with stirring, and the solid fraction was filtered off with suction.

The filtercake was washed with six times 60 g of a mixture of 92% by weight of glacial acetic acid and 8% by weight of acetic anhydride, and was suction-dried and dried in a stream of air at 100° C./65 mbar.

Yield: 147.3 g of 12F-biphenyltetracarboxylic dianhydride (82.2% of theory)

Melting point: 276°-278° C.

Anhydride group content, determined by titration with 0.1N sodium hydroxide solution/0.1N hydrochloric acid: 2.66 milliequivalents of anhydride/g (calculated 2.68)

Analysis for C$_{34}$H$_{14}$F$_{12}$O$_6$: calculated: C 54.70%; H 1.89%; F 30.54%. found: C 54.6%; H 2.0%; F 30.7%.

We claim:

1. A process for the preparation of a compound of the formula

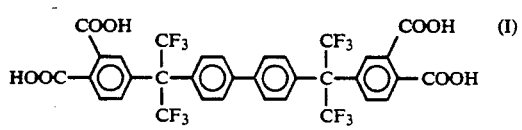

or the anhydride thereof by air oxidation in an acid medium at an elevated pressure and an elevated temperature in the presence of a catalyst mixture, which comprises oxidizing 4,4'-bis-[2-(3,4-dialkylphenyl)hexafluoroisopropyl]-biphenyl by passing aerial oxygen into an acid organic medium composed of a monocarboxylic acid having 1 to 4 carbon atoms, at a temperature of 120° to 220° C. and under a pressure of 5 to 40 bar in the presence of at least 2 heavy metal salts and also bromide ions, and isolating the product as claimed in formula I or converting the latter into the dianhydride of the compound of the formula (I), using acetic anhydride.

2. The process as claimed in claim 1, wherein the acid organic medium is composed of at least 40% by weight of acetic acid and/or propionic acid, relative to the total weight.

3. The process as claimed in claim 1, wherein the reaction temperature is 140° to 190° C.

4. The process as claimed in claim 1, wherein the oxidation is carried out under a pressure of 10 to 30 bar.

5. The process as claimed in claim 1, wherein the aerial oxygen employed for the oxidation has an oxygen content of more than 21% by volume, and the oxygen partial pressure of the oxygen at the inlet point is at least 1 bar.

6. The process as claimed in claim 1, wherein the oxygen partial pressure in the gas phase above the reaction medium is at least 0.2 bar.

7. The process as claimed in claim 1, wherein the heavy metal salts of cobalt, manganese and/or cerium are employed and these salts are used in the form of acetates.

8. The process as claimed in claim 1, wherein the bromine is employed in the form of bromides or as a solution of hydrogen bromide in water or glacial acetic acid.

9. The process as claimed in claim 1, wherein the molar ratio of cobalt to manganese is 3:1 to 1:3, the sum of the concentrations of the two elements cobalt and manganese being 0.01 to 0.20 gram.atom/kg of total reaction mass.

10. The process as claimed in claim 1, wherein the molar ratio of the sum of cobalt and manganese to bromine is 1:0.01 to 1:0.8.

11. The process as claimed in claim 1, wherein cerium is present in the catalyst as an additional metal ion, the molar ratio of the sum of cobalt and manganese to cerium being 1:0.02 to 1:1.2.

12. The process as claimed in claim 1, wherein the molar ratio of cobalt to cerium is 1:0.02 to 1:1.2.

13. The process as claimed in claim 1, wherein the reaction mixture is kept at 150° to 190° C. under an oxygen partial pressure of 0.4 to 2 bar for 1 to 3 hours after the completion of the exothermic reaction.

14. The process as claimed in claim 1, wherein the reaction is carried out at a concentration of water in the monocarboxylic acid of 2 to 12.

15. The process as claimed in claim 1, wherein the reaction temperature is 155° to 180° C.

16. The process as claimed in claim 1, wherein the oxidation is carried out under a pressure of 14 to 20 bar.

17. The process as claimed in claim 1, wherein the aerial oxygen employed for the oxidation has an oxygen content of more than 21% by volume, and the oxygen partial pressure of the oxygen at the inlet point is 3 to 10 bar.

18. The process as claimed in claim 1, wherein the oxygen partial pressure in the gas phase above the reaction medium is 0.35 to 2.8 bar.

19. The process as claimed in claim 1, wherein the oxygen partial pressure in the gas phase above the reaction medium is 0.45 to 1.3 bar.

20. The process as claimed in claim 1, wherein the molar ratio of cobalt to manganese is 3:1 to 1:3, the sum of the concentrations of the two elements cobalt and manganese being 0.02 to 0.12 gram.atom/kg of total mass.

21. The process as claimed in claim 1, wherein the molar ratio of cobalt to manganese is 3:1 to 1:3, the sum of the concentrations of the two elements cobalt and manganese being 0.04 to 0.08 gram.atom/kg of total mass.

22. The process as claimed in claim 1, wherein the molar ratio of the sum of cobalt and manganese to bromine is 1:0.05 to 1:0.4.

23. The process as claimed in claim 1, wherein cerium is present in the catalyst as an additional metal ion, the molar ratio of the sum of cobalt and manganese to cerium being 1:0.05 to 1:0.6.

24. The process as claimed in claim 1, wherein the reaction is carried out at a concentration of water in the monocarboxylic acid of 2 to 7% by weight.

25. The process as claimed in claim 1, wherein the reaction is carried out at a concentration of water in the monocarboxylic acid of 3 to 5% by weight.

* * * * *